United States Patent [19]
Ericson et al.

[11] Patent Number: 6,086,753
[45] Date of Patent: Jul. 11, 2000

[54] SYSTEM FOR ELIMINATING GASES IN A CONTAINER

[75] Inventors: Björn Ericson; Ji Jun Fang; Sture Hobro; Erik Linderup, all of Lund, Sweden

[73] Assignee: Gambro Med Tech AB, Sweden

[21] Appl. No.: 09/171,055

[22] PCT Filed: Apr. 10, 1997

[86] PCT No.: PCT/SE97/00593

§ 371 Date: Jan. 14, 1999

§ 102(e) Date: Jan. 14, 1999

[87] PCT Pub. No.: WO97/38743

PCT Pub. Date: Oct. 23, 1997

[30]     Foreign Application Priority Data

Apr. 12, 1996 [SE] Sweden .................................. 9601379

[51] Int. Cl.⁷ ............................. B01D 17/12; B01D 19/00
[52] U.S. Cl. .................... 210/120; 210/188; 210/321.71; 210/647; 96/155; 96/156; 137/88; 422/261
[58] Field of Search ............................... 210/86, 120, 188, 210/321.71, 541, 542, 646, 647, 96.1, 96.2, 143; 96/155, 156, 157; 95/241, 8; 422/261; 137/87.1, 88, 102; 366/150.1, 151.1, 152.4, 160.7

[56]           References Cited

U.S. PATENT DOCUMENTS 4,784,495  11/1988  Jonsson et al. ......................... 210/647

5,779,357   7/1998  Jonsson et al. ............................ 137/88

FOREIGN PATENT DOCUMENTS

| 0 278 100 A2 | 8/1988 | European Pat. Off. . |
| 2237639 | 2/1975 | France ................................ 210/321.71 |
| 2625025 | 10/1977 | Germany ........................... 210/321.71 |
| 55-115819 | 9/1980 | Japan . |

OTHER PUBLICATIONS

Dialog Information Services, File 350, Dialog accession No. 002556364, WPI accession No. 80–74387C/42, Nissho KK: "Bicarbonate–type dialysis soln. mfr,–includes heating and degassing the diluting soln. and opt. the conc. solns. prior to mixing" & JP,A, 55115819, 800906, 8042 (Basic), Undated.

*Primary Examiner*—Joseph W. Drodge
*Attorney, Agent, or Firm*—Lerner, David, Littenberg, Krumholz & Mentlik, LLP

[57]                ABSTRACT

Apparatus for removing gases from a container used to prepare concentrates of a powder in water are disclosed including a supply conduit for supplying water to the container, a removal conduit for removing the concentrate from the container, a pump including a negative pressure side, an evacuation conduit for connecting the negative pressure side of the pump with the container, an actuatable valve disposed in the evacuation conduit whereby upon actuation the actuatable valve connects the container with the negative pressure side of the pump, an indicator for indicating when the container includes a predetermined amount of the gases, and a control mechanism for actuating the valve in response to the indicator to eliminate the gases from the container.

11 Claims, 7 Drawing Sheets

SYSTEM FOR ELIMINATING GASES IN A CONTAINER

This application is a 371 of PCT/SE97/00593, filed on Apr. 10, 1997.

FIELD OF THE INVENTION

The present invention relates to an improvement in a dialysis machine of the type which is described in European Patent No. 278,100 which corresponds to the dialysis machine known as GAMBRO AK 100.

BACKGROUND OF THE INVENTION

In a dialysis machine of the above-mentioned type, one or more cartridges containing sodium bicarbonate powder, sodium chloride or other salts are used. The salt is dissolved by the introduction of water into the cartridge and removal of concentrate from the cartridge. The concentrate is used to prepare the intended dialysis solution.

The composition of the dialysis solution is determined in the dialysis machine by measuring the conductivity of the prepared solution and regulating dosage pumps for each of the various concentrates. It is now common to use two different concentrates; a B-concentrate comprising only bicarbonate from the above-mentioned bicarbonate cartridge, and an A-concentrate comprising the remaining components in concentrated form, for example to a 37-fold concentration. Other combinations of concentrates also exist, such as the B-concentrate, which besides bicarbonate, may also comprise sodium chloride. Alternatively, the B-concentrate can be divided into two parts comprising bicarbonate and sodium chloride, respectively, whereby the A-concentrate comprises the remaining components in a more concentrated form.

By preparing the bicarbonate concentrate and, where appropriate, the sodium chloride concentrate on demand in the dialysis machine, an advantage is realized in that the bicarbonate concentrate remains stable until it is used in a dialyser connected to the dialysis machine.

If a dialysis solution is prepared in advance, which is also now a common procedure, the risk exists that the bicarbonate can decompose to carbon dioxide and carbonate. This implies that the pH value for the solution rises and the risk of precipitation of the calcium carbonate arises during mixing to the prepared dialysis solution. This can affect the final composition of the dialysis solution (reduction of the calcium ion concentrate) as well as creating problems of silting up of conduits and components in the dialysis machine due to the deposition of calcium carbonate. For these reasons, the bicarbonate cartridge as described above has attained widespread use.

As mentioned above, the dialysis solution is prepared by mixing the two concentrates with water. The mixing process is regulated by conductivity meters which control various dosage pumps. Conductivity meters are, however, sensitive to possible incorporation of gas bubbles in the solution. Thus, the conductivity meters are generally preceded by gas separators whereby more accurate, less fluctuating measuring values can be obtained.

The dialysis machine is provided with a monitoring system which is separated from the regulating system and serves to emit alarm signals should error situations arise. In the above-mentioned dialysis machine; namely, GAMBRO AK 100, monitoring of the dosage of concentrate occurs by monitoring the number of revolutions of the dosage pumps. If the number of revolutions differs too greatly from an expected value, an alarm signal is emitted.

When using the above-mentioned bicarbonate cartridge containing dry bicarbonate powder, it is necessary that the powder be wetted with water prior to use. This takes place in a particular "priming step". Water is introduced into the cartridge at its upper end at the same time that a substantial vacuum is applied to the lower end of the cartridge. Water thus fills substantially the entire cartridge in less than a minute.

When a sensor positioned downstream of the bicarbonate cartridge detects that primarily concentrate is flowing from the cartridge, the sensor indicates that the priming step is complete. A valve then switches over the machine so that the substantial vacuum is terminated. This sensor can be the above-mentioned conductivity meter.

During the priming step, a small quantity of air or gas is normally trapped at the upper end of the cartridge. This quantity of gas does not, however, normally affect the functioning of the cartridge. In the above-mentioned European Patent No. 278,100, various methods are described for removing this quantity of gas before the dialysis treatment commences, i.e. during the priming step.

However, it sometimes occurs that the trapped gas in the upper region of the cartridge increases in volume during the dialysis treatment. If the trapped volume of gas becomes so great that a considerable quantity of gas passes out through the outlet of the cartridge and reaches the conductivity meter, an alarm is raised. Furthermore, it will be appreciated that the normal functioning of the cartridge is greatly affected if far too great a volume of gas is present in the cartridge. Normally, it is preferred that the water level always remains above the salt particle level in the cartridge.

The above-mentioned condition with increasing volume of gas can be attributed to several causes. One possible cause is leakage in the connection between the upper or lower ends of the cartridge and the dialysis machine. The dialysis machine normally maintains a small vacuum in the cartridge. Another such cause can be that gas bubbles accompany the water which enters the cartridge and thereafter become separated in the cartridge. The principal cause would seem, however, to be gas formation in the cartridge, such as formation of carbon dioxide gas.

It has been observed that the above-mentioned problem is exacerbated at higher ambient temperatures, which is probably due to the decomposition of bicarbonate to carbon dioxide and carbonate.

Since the cartridge circuit is closed, there is no other route for the gas to flow than through the outlet from the cartridge, something which can activate the above-mentioned conductivity alarm. In order to deal with such an alarm situation, it is then necessary to remove the bicarbonate cartridge and to insert a new cartridge into the system, whereafter the machine has to be restarted with a priming step and subsequent stabilising steps, something which can take a long period of time. During this time, the dialysis treatment has to be interrupted.

It has also been observed that the conductivity signal from the conductivity meter, despite the preceding gas situation, fluctuates greatly, particularly at high ambient temperatures. In extreme cases, such as at high temperatures, these fluctuations are so great that the alarm limit is exceeded.

It is noted that Japanese Patent No. 55115819 describes a method of degassing the water, and also possibly the concentrates, prior to mixing at volumetric dilution in order to avoid problems relating to air bubbles being formed during heating.

SUMMARY OF THE INVENTION

One object of the present invention is to provide a system which overcomes the above-mentioned problems associated with gas-filling in a bicarbonate cartridge.

Another object of the present invention is to provide an indicating arrangement for indicating when a dialysis cartridge runs the risk of becoming full of gas and measures are required in order to remove this gas.

A further object of the present invention is to improve the priming of a dialysis cartridge.

In accordance with the present invention, these and other objects have now been realized by the discovery of apparatus for the elimination of gases from a container including an upper end and a lower end for preparing a concentrate of a powder in water, the apparatus comprising a supply conduit for supplying water to the container, a removal conduit for removing the concentrate from the container, a pump including a negative pressure side, an evacuation conduit for connecting the negative pressure side of the pump with the container, an actuatable valve disposed in the evacuation conduit whereby upon actuation said actuatable valve connects the container with the negative pressure side of the pump, an indicator for indicating when the container includes a predetermined amount of the gases, and control means for actuating the valve in response to the indicator to eliminate the gases from the container. In accordance with a preferred embodiment, the powder comprises a bicarbonate powder and the concentrate comprises a dialysis solution.

In accordance with one embodiment of the apparatus of the present invention, the actuatable valve comprises a three-way valve normally connecting the supply conduit to the upper end of the container. Preferably, the three-way valve is disposed in proximity to the upper end of the container.

In accordance with another embodiment of the apparatus of the present invention, the actuatable valve includes at least three connections, and the evacuation conduit includes a first evacuation conduit portion connecting the supply conduit to one of the at least three connections, a second evacuation conduit portion connecting the removal conduit to another of the at least three connections, and a third evacuation conduit portion connecting the negative pressure side of the pump to another of the at least three connections, whereby the actuatable valve normally connects the third evacuation conduit portion to the second evacuation conduit portion, and upon actuation, the actuatable valve connects the third evacuation conduit portion to the first evacuation conduit portion.

In a preferred embodiment, the supply conduit includes a constriction disposed in the supply conduit distal from the first evacuation conduit portion with respect to the upper end of the container.

In another embodiment, the apparatus includes a supply conduit valve disposed in the supply conduit distal from the first evacuation conduit portion with respect to the upper end of the container, the supply conduit valve being normally open but being closable upon actuation during the elimination of the gases.

In accordance with another embodiment of the apparatus of the present invention, the apparatus includes a gas separator in the removal conduit, the gas separator including a gas level indicator for indicating a predetermined level of gas in the gas separator. In a preferred embodiment, the gas separator comprises a chamber having a predetermined cross-sectional area, an inlet proximate to the lower end of the container, and an outlet distal from the lower end of the container, the cross-sectional area of the chamber being substantially greater than the area of the removal conduit whereby the flow velocity through the chamber is substantially lower than the flow velocity through the removal conduit and gas separation takes place therein. Preferably, the apparatus includes a concentrate dosage pump disposed in the removal conduit downstream of the gas separator with respect to the container.

BRIEF DESCRIPTION OF THE DRAWINGS

The present invention will be described below in greater detail with reference to the detailed description which follows, and which, in turn, refers to the attached drawings, in which.

DETAILED DESCRIPTION

Figure 1:
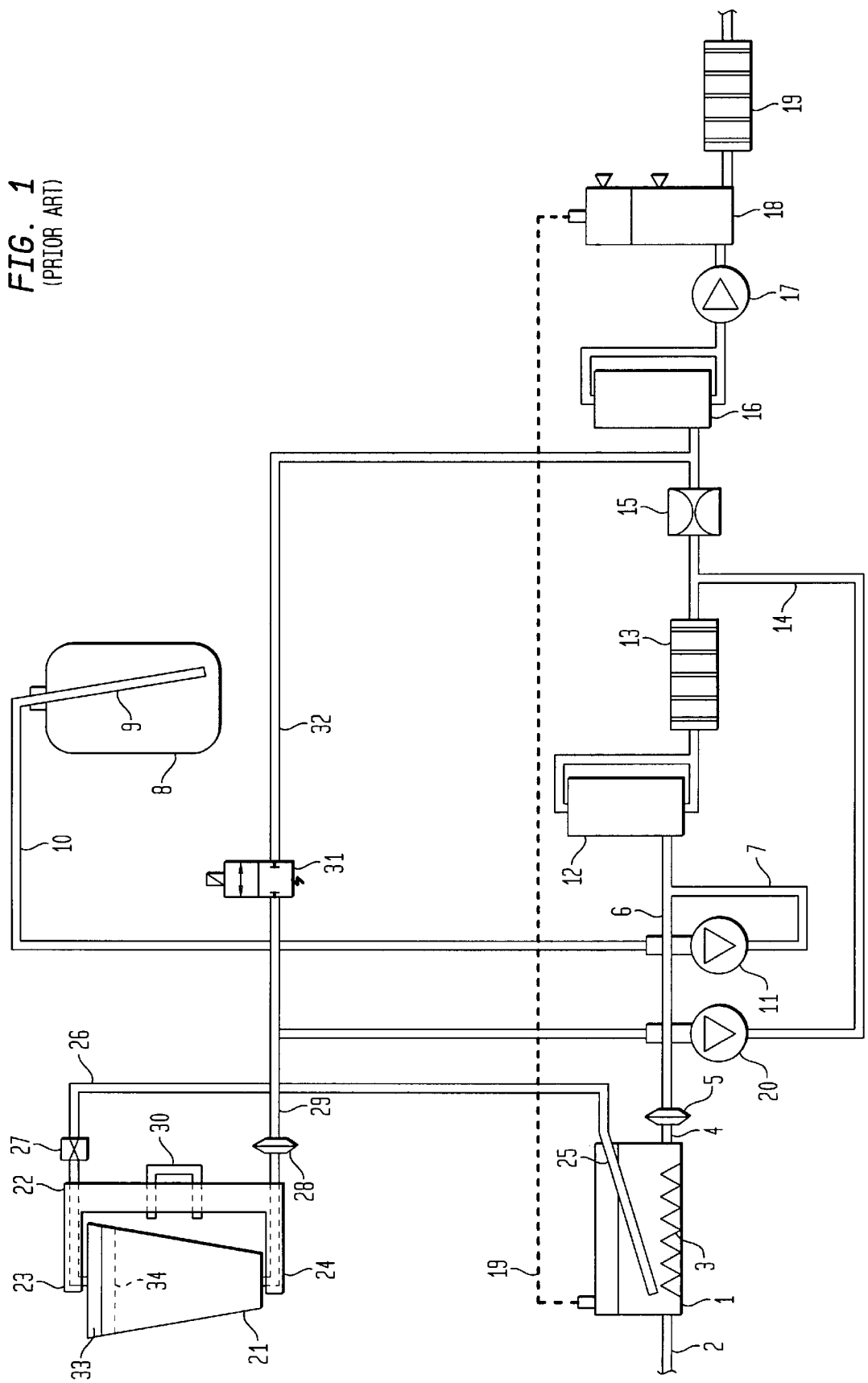
FIG. 1 is a schematic diagram of a dialysis machine according to the prior art, corresponding essentially to the dialysis machine known as GAMBRO AK 100.

A dialysis machine is shown schematically in FIG. 1, corresponding substantially to the dialysis machine sold as GAMBRO AK 100. The dialysis machine comprises a water reservoir 1 with inlet 2 for water which is normally received from a water purification plant (RO-unit, reverse osmosis).

The water reservoir 1 contains a heating coil 3 which warms the water to a suitable temperature, usually about 37° C. An outlet 4 is connected through a particle filter 5 to a primary conduit 6 for preparation of the dialysis solution.

A first branch conduit 7 supplies A-concentrate from a container 8 by means of a suction nozzle 9 inserted in the container, a conduit 10 and a dosage pump 11. The A-concentrate is mixed with water in the conduit 6 and is supplied to a mixing chamber 12 where homogenisation of the mixture takes place. Thereafter, the mixture passes a conductivity meter 13 where the conductivity of the mixture is determined. The conductivity meter 13 controls the dosage pump 11 so that a predetermined conductivity is attained. Normally, the A-concentrate is diluted approximately in the proportion of about 1:34.

A second branch conduit 14 is located downstream of the conductivity meter 13, which conduit supplies concentrated bicarbonate or B-concentrate. The thus obtained dialysis solution passes through a throttle valve 15 and further to an expansion chamber 16 and a powerful pump 17. The dialysis solution is fed from the pump 17 to a bubble chamber 18 and a second conductivity meter 19. The increase of the conductivity with respect to the conductivity meter 13 is determined by the conductivity meter 19 and the difference signal regulates a dosage pump 20 for bicarbonate concentrate.

The throttle arrangement 15 and the pump 17, together with the expansion chamber 16, form a gas eliminator. Downstream of the throttle arrangement 15, the pressure is relatively low; i.e., around −600 mmHg; and any gas in the solution is released, which is assisted by the expansion chamber 16. The released gas collects in bubbles and passes through the pump 17 to the bubble chamber 18. The received bubbles rise to the upper part of the chamber 18 and are removed at approximately atmospheric pressure.

Bicarbonate concentrate is prepared in the above-depicted dialysis machine in situ by use of a cartridge containing bicarbonate powder. The cartridge 21 is connected to a particular cartridge holder 22 equipped with swinging arms 23 and 24, as is described in greater detail in European Patent No. 278,100. The cartridge 21 is connected in a circuit which runs from the water reservoir 1 through a suction nozzle 25 inserted in the water reservoir, a conduit 26 and a throttle arrangement 27 to the upper arm 23 of the cartridge holder 22. The upper arm 23 is connected to the upper end of the cartridge 21 by means of a spike. The lower end of the cartridge is, in a similar manner, connected to the lower arm 24 and communicates further through a particle filter 28 and a conduit 29 with the dosage pump 20 for bicarbonate concentrate.

The dialysis machine can also be used for B-concentrate in liquid form by swinging the arms 23 and 24 to a shunt conduit 30, with the suction nozzle 25 being placed in a container for B-concentrate in a manner similar to that of the suction nozzle 9.

In order to initially wet the powder in the cartridge 21, the dialysis machine is provided with a priming arrangement in the form of a conduit 32 and a valve 31. The conduit 32 is connected between the lower end of the cartridge, preferably between the filter 28 and the pump 20, and the primary conduit 6 downstream of the throttle arrangement 15 where a substantial vacuum is present (e.g., about −600 mmHg).

Priming takes place by placing a bicarbonate cartridge 21 in the holder 23, 24, 22, as shown in FIG. 1, and opening valve 31. In this manner, a substantial vacuum is applied to the cartridge 21 which draws air out of the lower end of the cartridge until the pressure in the cartridge is in the order of about −600 mmHg.

At the same time, water is drawn from the water reservoir 1 through conduit 26 and throttle arrangement 27 into the upper end of the cartridge. By means of the throttle arrangement 27, it is ensured that low pressure can be established in the cartridge before water flows in through arm 23. Thereafter, the cartridge is filled from above with water which is drawn through the powder in the cartridge 21 and eventually reaches the outlet in the arm 24. This condition is detected by the conductivity meter 19, whereupon valve 31 is closed.

Concentrate pump 20 is operated during the entire process. The concentrate pump 20 now receives liquid-based concentrate from the cartridge 21. A closed circuit has thus been created from the water reservoir 1 through the conduit 26, the cartridge 21 and the conduit 29 to the pump 20.

During the above-mentioned process, a certain quantity of air will have become trapped in the upper end of the cartridge in a space 33. However, the water level is above the level of the bicarbonate powder 34 so that the powder is constantly wet. During operation, bicarbonate concentrate is removed through the concentrate pump 20. Due to the closed circuit, as much water is supplied to the upper end of the cartridge as is removed from its lower end. The supplied water dissolves the bicarbonate powder and a substantially saturated solution is formed in the cartridge. When the solution is saturated, dissolution ceases automatically.

Since the cartridge 21 is included in a closed circuit, the gas in the space 33 remains entrapped and cannot migrate anywhere. This is not a disadvantage and does not lead to any damage.

In the event that a slight vacuum is present in the cartridge 21, any leak in the connection between the cartridge 21 and the upper arm 23 can result in an increase in the gas volume in the space 33.

The gas volume can also increase by means of gas accompanying the water from the water reservoir 1 through the conduit 26 to enter the cartridge 21.

At high ambient temperatures the sodium bicarbonate solution in the cartridge can to a certain extent decompose to carbon dioxide and sodium carbonate (soda). Such carbon dioxide gas can also collect in the space 33 and increase the confined gas volume.

The gas volume in the space 33 is only harmful if it becomes too great and forces the water level below the level of the powder 34. In that case there is a risk that the concentrated, substantially saturated solution which is removed through the outlet in the arm 24 can contain a certain quantity of gas. The cartridge may even run dry, whereby a large quantity of gas will exit through the outlet 24. This condition can create an alarm. If the cartridge runs dry, it must normally be replaced, which can thus cause an interruption in operation.

In accordance with the present invention, it is proposed to provide the dialysis machine with a valve with which the gas volume in the space 33 can be reduced, particularly if it shows a tendency to increase and to become far too great, i.e. drop below the level of the powder concentrate 34.

Figure 2:
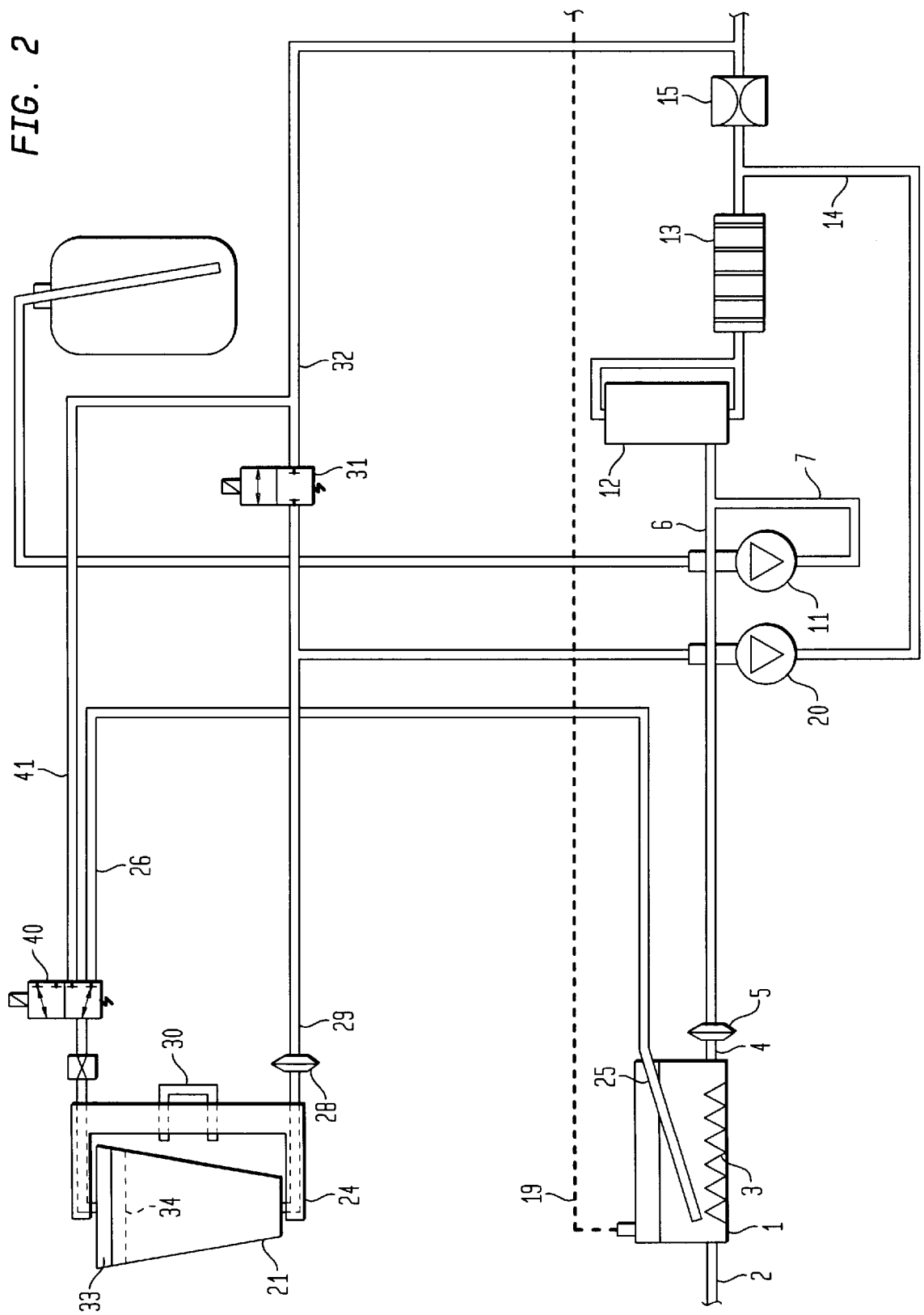
FIG. 2 is a schematic diagram corresponding to FIG. 1 with a deaeration device according to the present invention.

A first embodiment of the present invention is shown in FIG. 2. A three-way valve 40 which normally connects the upper end of the cartridge 21 to the water reservoir 1 is placed in the conduit 26. In its second, activated position, however, the valve 40 connects the upper end of the cartridge 21 to a conduit 41 which leads to a substantial vacuum downstream of the throttle arrangement 15, i.e. to the conduit 32.

When the valve 40 is switched over, the air in the upper end of the cartridge 21 is drawn through the valve 40, the conduit 41 and the conduit 42 to the pump 17 and is separated in the subsequent bubble chamber 18 (see FIG. 1). By arranging the valve 40 as close as possible to the cartridge 21, only a small quantity of water has first to flow through the conduits 41 and 32 before the air is drawn out. In this manner, a substantial vacuum is established in the cartridge 21.

When the valve 40 is returned to its initial position, the vacuum in the upper end of the cartridge 21 will result in water being drawn in through the conduit 26 from the water reservoir 1, partially filling the space 33 in order to equalise the vacuum.

In this manner, the air-filled space 33 can be substantially halved with the help of a vacuum of about a half atmosphere. Since the valve 40 is located close to the inlet of the cartridge, the effect of the pressure reduction and subsequent pressure equalisation with water will be as great as possible. It is possible to repeat this process several times, for example 3 times in the course of one minute.

This deaeration of the cartridge 21 can occur at repeating time intervals during dialysis treatment, for example in connection with a regularly repeating calibration of the ultrafiltration sensor in the dialysis machine, which normally occurs at 30-minute intervals. The deaeration may result in a conductivity alarm since the large quantity of gas which flows through the conduit 32 and pump 17 can result in the flow in the primary conduit 6 being affected to such a degree that the alarm limits are exceeded. Should the machine be in its calibration mode, however, the alarm can be suppressed.

Figure 3:
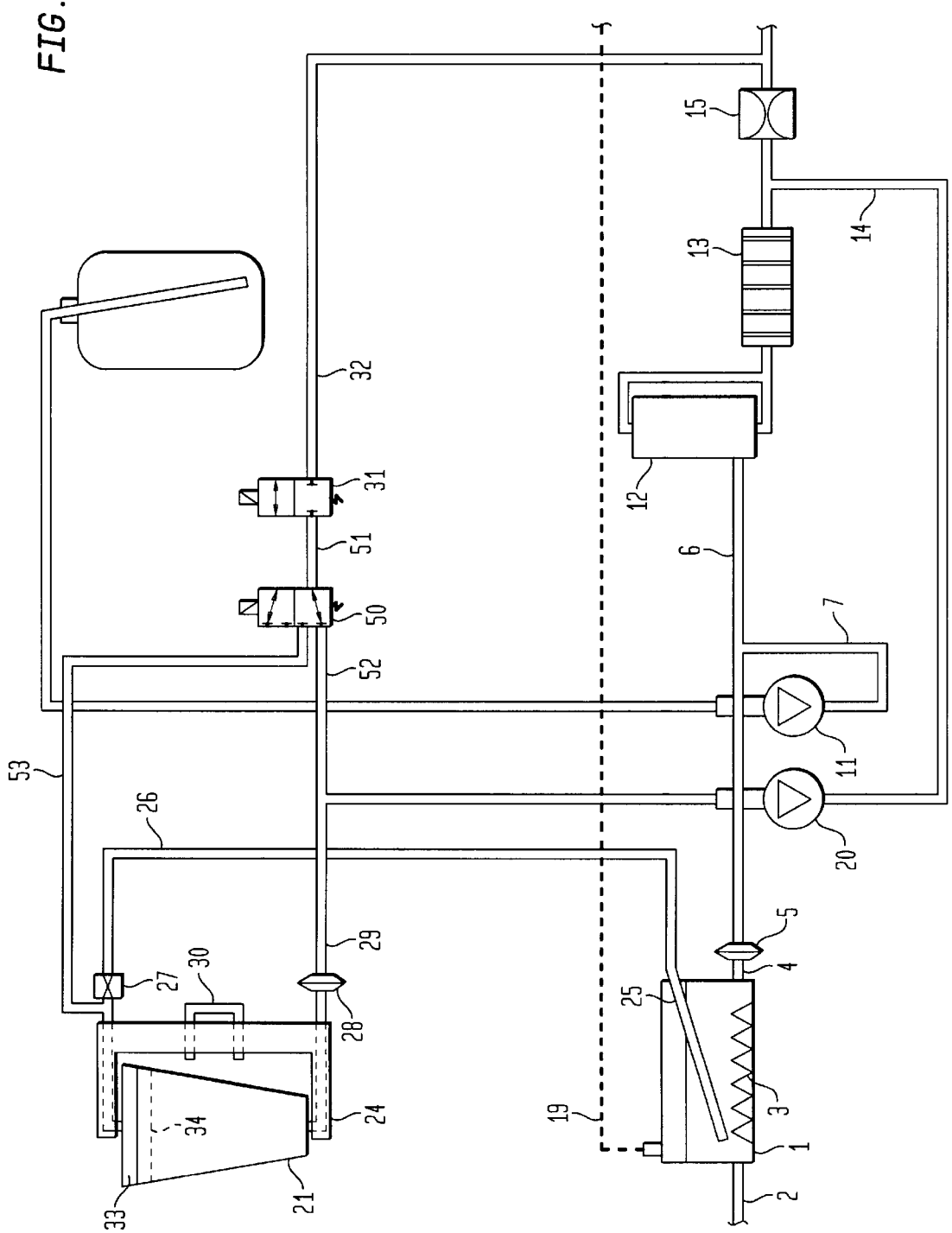
FIG. 3 is a schematic diagram corresponding to FIG. 1 showing an alternative embodiment of the deaeration device according to the present invention.

The embodiment shown in FIG. 2 has a minor drawback in that any leakage in the valve 40 between the conduit 26 and the conduit 41 can disrupt the functioning of the dialysis machine. One embodiment of the present invention in which this drawback is overcome is shown in FIG. 3. In this embodiment the three-way valve 50, which corresponds to the three-way valve 40 in the embodiment according to FIG. 2, is placed in the conduit 32 between the priming valve 31 and the connection to conduit 29.

The deaeration valve 50 is thus connected to the valve 31 by means of a conduit 51 and to the conduit 29 through a conduit 52. The valve 50 connects the conduit 51 to the conduit 52 in its normal position. In its activated position the valve 50 connects the conduit 51 to a deaeration conduit 53 which is connected in the conduit 26 between the throttle arrangement 27 and the inlet to the cartridge 21.

By means of this connection, it is ensured that no substantial pressures are present across the deaeration valve 50 during normal operation. The valve 31 isolates the system from the substantial vacuum in conduit 32.

The deaeration takes place by switching the deaeration valve 50 to its activated position, whereafter the valve 31 is opened. In this manner, a substantial vacuum arises in the conduit 53 through the valve 50, the conduit 51, the valve 31 and the conduit 32. A suction pressure thus arises in the conduit 26 at the connection to the conduit 53. Air will thus be drawn from the upper end of the cartridge 21. At the same time, water flows from the water reservoir 1 by means of the conduit 26 and the throttle arrangement 27 to the conduit 53. Due to the throttle arrangement 27, there is still, however, a substantial vacuum in the upper end of the cartridge 21. Thereafter, the valve 31 is closed whereby water flows from the water reservoir 1 through the conduit 26, the throttle arrangement 27 and to the upper end of the cartridge 21 to equalise the vacuum therein. The valve 31 can thereafter be opened for a second deaeration cycle if so desired.

An alternative method of operating the deaeration arrangement according to FIG. 3 is the following. Firstly, the valve 50 is switched to its activated position, whereafter the valve 31 is opened and a substantial vacuum is established in the upper end of the cartridge 21. Thereafter, the valve 50 is switched to its normal position whereby the substantial vacuum is diverted to the conduit 29 which is connected to the lower end of the cartridge 21. In this manner, water flows from the water reservoir 1 through the conduit 26, the throttle arrangement 27 and into the upper end of the cartridge 21. The valve 50 is thereafter switched back to its activated position and further gas is withdrawn from the upper end of the cartridge 21 by means of the conduit 53. This process is repeated one or more times. Finally, normal operation is resumed by switching the valve 50 to its normal position and closing the valve 31. The advantage of this method is that the powder in the cartridge 21 is agitated and any gas bubbles which adhere to the powder are loosened and rise to the upper end of the cartridge 21. At the same time, any channel formations in the powder in the cartridge can be avoided.

A combination of the two above-described methods can also be used in which the valve 13 is closed between each switching action of the valve 50 to permit equalisation of the pressure in the cartridge 21 by means of the conduit 26 before the vacuum is applied to the lower end of the cartridge by means of the conduit 29.

Figure 4:
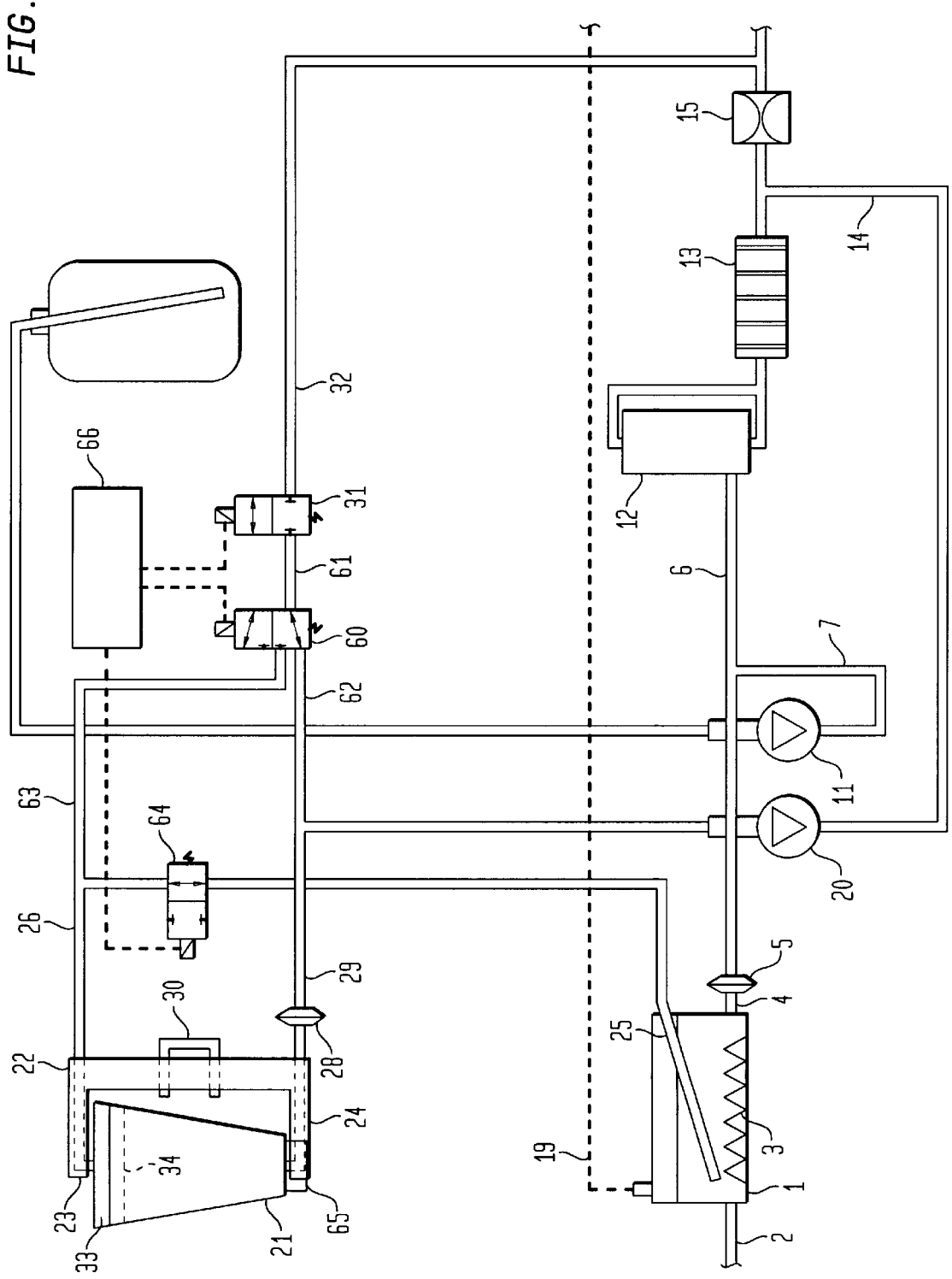
FIG. 4 is a schematic diagram corresponding to FIG. 1 showing a variant of the embodiment of the present invention according to FIG. 3.

An alternative embodiment to that of FIG. 3 is shown in FIG. 4. Since the throttle arrangement 27 is normally positioned very close to the inlet to the cartridge 21, it can be difficult to connect the conduit 53 downstream of the throttle arrangement 27.

In the embodiment which is shown in FIG. 4, the conduit 63 from the valve 60 has been connected to the conduit 26, and the throttle arrangement 27 has been removed. A normally open valve 64 is connected in conduit 26 between the water reservoir 1 and the connection to the conduit 63. The valve 60 is connected to the valve 31 by means of a conduit 61 and is connected to the conduit 29 by means of a conduit 62.

During connection of the valve 60, the valve 64 is closed, and in this manner water cannot be withdrawn from the water reservoir through conduit 26 to conduit 63. Otherwise, the operation is the same as for the operation according to the embodiment of FIG. 3. In the embodiment of FIG. 4, operation of the throttle arrangement 27 is replaced by operation of valve 60.

As has been stated above, the deaeration valves 40, 50, 60 can be activated on those occasions when it is desired to deaerate the bicarbonate cartridge 21. Such deaeration can take place regularly in 30-minute intervals during the dialysis treatment, when the normal dialysis treatment is interrupted for a calibration step. It is also possible to provide the dialysis machine with the capability of manual initiation of deaeration. This can occur should a nurse or other user discover that the water level has dropped below the level of the powder 34 in the cartridge 21, or when the trapped volume of gas becomes too great.

It is also feasible to provide the holder 22 with an arrangement which senses if the water level drops below the level of the indicator. Such an indicator could be a load-cell 65 as illustrated in FIG. 4. In FIG. 4 there is additionally shown an electronic device 66 or microprocessor which controls the function of the valves, as indicated by dashed lines in FIG. 4. Device 66 can be adapted to control or indicate when deaeration is required, for example at regular time intervals or according to signals from an indication device or upon demand from a user.

Figure 5:
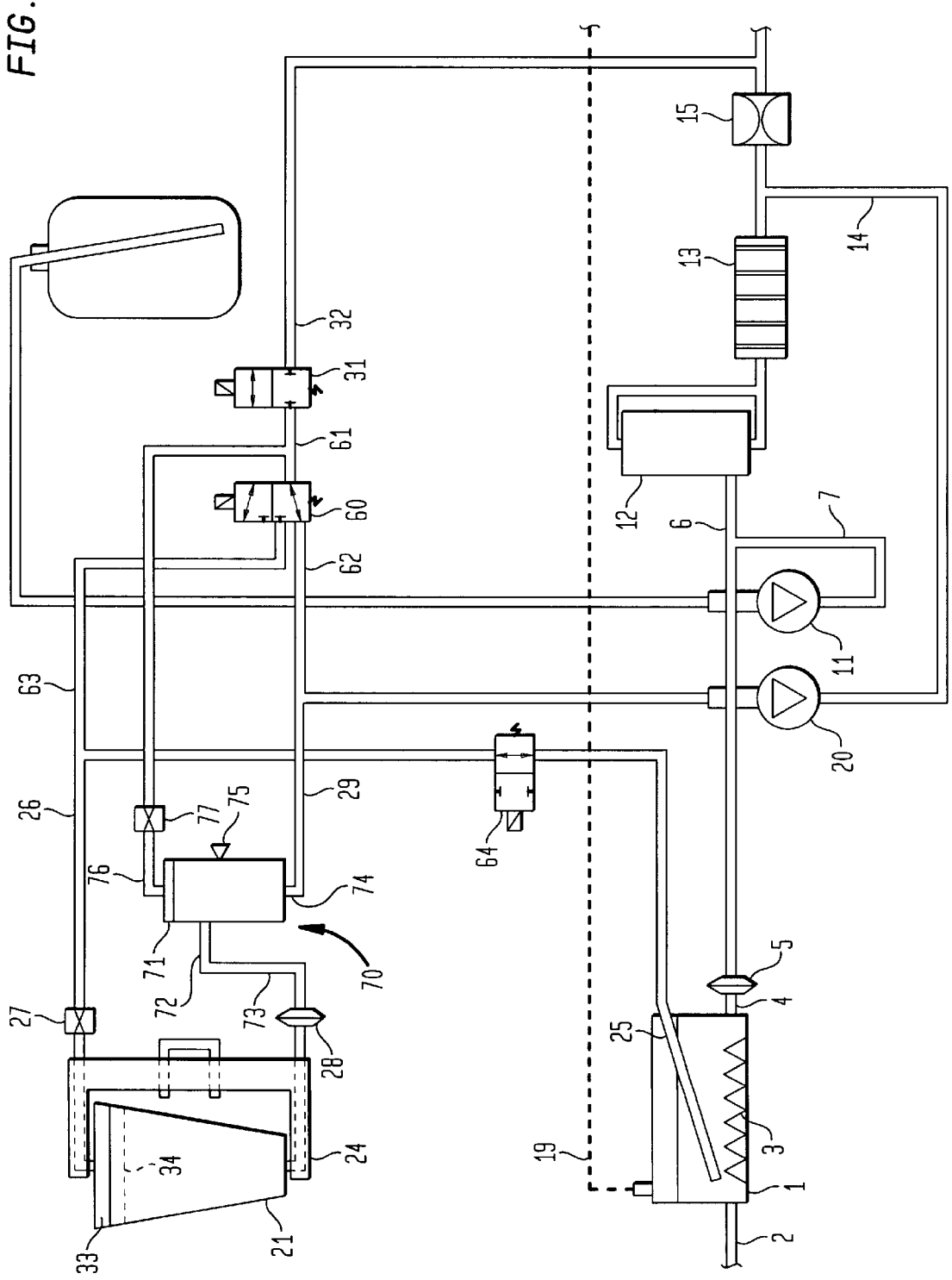
FIG. 5 is a schematic diagram corresponding to FIGS. 3 or 4, provided with an indicator.

A further indication arrangement is shown in FIG. 5. The embodiment according to FIG. 5 is provided with the same valves and conduits as the embodiment according to FIG. 4. In addition, the conduit 29 which connects the outlet of the cartridge 21 to the dosage pump 20 is provided with a deaeration indicator 70 in the form of a gas separation chamber 71.

The chamber 71 is provided with an inlet 72 connected to the outlet from the cartridge 21 through a conduit 73, and to an outlet 74 connected to the conduit 29 and further to the pump 20. The chamber 71 may be positioned anywhere along the conduit 29 between the outlet from the cartridge 21 and the dosage pump 20.

The bicarbonate concentrate from the cartridge 21 thus flows to the chamber 71, which has a relatively large cross section. Due to the low flow velocity in the chamber 71, any gas bubbles in the concentrate are separated and rise to the upper end of the chamber 71. If the bicarbonate concentrate should contain a large quantity of small gas bubbles, such as can be the case at high ambient temperatures, the confined gas volume in the chamber will increase. When the gas volume or the water level in the chamber 71 reaches an indicator 75, a signal is emitted which indicates that deaeration is required.

If the cartridge 21 runs dry so that the space 33 increases greatly in volume and the risk arises that gas will be drawn out together with the concentrate, the gas which accompanies the concentrate will quickly fill the chamber 71 so that the level indicator 75 is activated.

The chamber 71 preferably has a volume which is large enough such that the quantity of concentrate which is accommodated beneath the indicator 75 is sufficient for, for example, several minutes' treatment; i.e. about 50 ml. If the cartridge has run dry, the dialysis treatment can thus continue for several minutes in anticipation of a suitable occasion for deaeration.

When the level indicator 75 registers that deaeration is required, the valves 60, 31 and 64 are activated as described above in connection with the embodiment according to FIG. 4. In addition, the chamber 71 is provided with a conduit 76 which connects the upper gas-filled end of the chamber with the conduit 61 between the valve 60 and the valve 31. Furthermore, the conduit 66 is provided with a throttle arrangement 77. When the deaeration cycle is activated by activating the valve 60 and the valve 31 is opened, the upper end of the chamber 71 will thus be evacuated by the conduit 76, conduit 61, the valve 31 to the conduit 32. When the water level in the chamber 71 has risen such that water fills the conduit 76 and reaches the throttle arrangement 77, the flow through the conduit 76 will be very small. At termination of the deaeration cycle, the chamber 71 will therefore be substantially full of liquid and a new monitoring cycle can be initiated by means of the chamber 71.

During normal operation, bicarbonate concentrate flows from the cartridge 21 through conduit 73 and chamber 71 to the conduit 29 and the concentrate pump 20. It has been shown that the conductivity measurement in the conductivity meter 19 attains considerably smaller fluctuations downstream of the connection of chamber 71. The reduction of the fluctuations is already noticeable at a room temperature of 20° C. and becomes even more marked at room temperatures in the order of 30° C., something which can arise in warm countries.

One explanation for the above-mentioned fluctuations and the decrease when the chamber 71 is connected can be the following. At higher ambient temperatures, carbon dioxide gas is formed in the cartridge 21 at the same time as dissolution of the powder, or during the period substantially saturated concentrate is in the cartridge 21 before being fed through the outlet to the conduit 29. As the concentrate is fed out, the smallest bubbles, which do not adhere to adjacent salt particles, accompany the concentrate. The quantity of gas bubbles in the exiting concentrate varies stochastically. At higher temperatures, the mixture is greater and, as a result, so too is the variation of the mixed gas bubbles. The pump 20 is a metering pump which pumps a predetermined quantity of concentrate per revolution or fraction of a revolution. Since the concentrate is, however, diluted with gas bubbles, different quantities of sodium bicarbonate will pass through the pump depending on the intermixed quantity of gas. The intermixed quantity of gas is thereafter effectively separated in the bubble chamber 18. The conductivity meter 19 is thus subjected to a varying concentration where the variation depends on the quantity of intermixed gas bubbles during the passage of the pump 20. The more gas bubbles which are intermixed, the lower the concentration of the bicarbonate becomes.

By introducing a bubble separator or gas separator 71 before the metering pump 20, it is ensured that the pump 20 always pumps saturated concentrate which is not diluted with gas bubbles. Consequently, the feeding of bicarbonate to the primary conduit 60 will be very consistent and without fluctuations, and as such the conductivity meter 19 emits a very constant signal.

Figure 6:
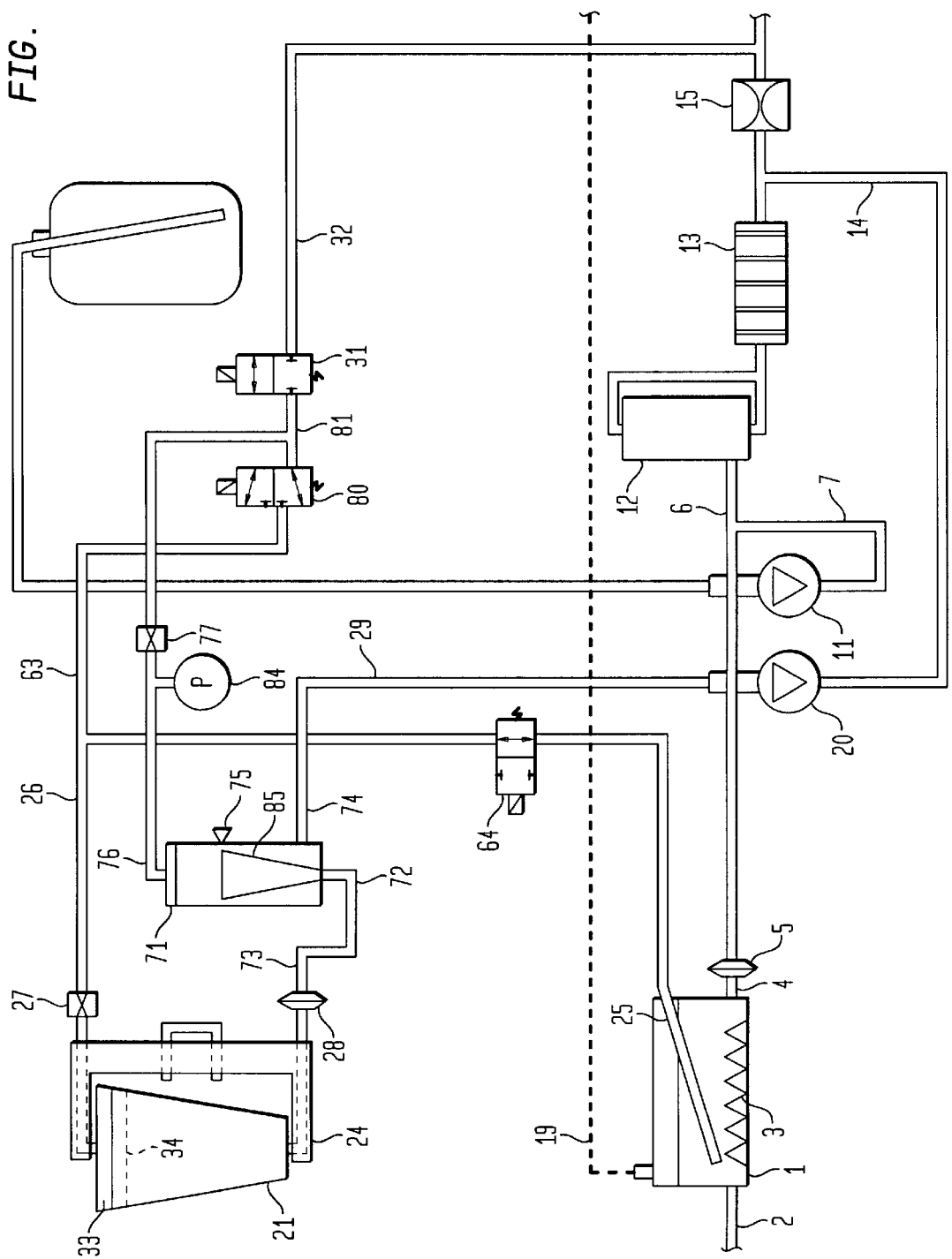
FIG. 6 is a schematic diagram corresponding to FIG. 5 showing an alternative embodiment of the present invention.

A further embodiment of the present invention is shown in FIG. 6 which is a variation of the embodiment according to FIG. 5. The switching valve 60 has in this case been replaced by a simple valve 80 and the conduit 62 has been omitted.

In this embodiment, priming of the cartridge 21 takes place by opening the valve 31 while the valve 80 is closed and the valve 64 is in its normal open position. In this manner, a substantial vacuum is obtained in the cartridge 21 through conduit 73, the chamber 71, the conduit 76, the throttle arrangement 77, the conduit 81, the valve 31 and the conduit 32. Water flows from the water reservoir 1 through valve 64 and the conduit 26 and the throttle arrangement 27 to the upper end of the cartridge 21. Water is thus introduced into the upper portion of the cartridge 21 and is withdrawn from the lower portion and the conduit 73 and fills the chamber 71. At the same time, the pump 20 is running, thus causing the liquid to flow through the outlet 74 to the conduit 29 and the pump 20. Simultaneously, the air in the upper end of the chamber 71 is withdrawn through conduits 76 and 81. When the entire chamber 71 is filled with concentrate, the conduit 76 is filled up to the throttle arrangement 77 with concentrate. When liquid reaches the throttle arrangement 77, the pressure drop over the throttle arrangement falls substantially, which is sensed by a pressure sensor 84 arranged in connection with the conduit 76. The pressure sensor 84 indicates that priming has been achieved and the valve 31 is closed. The cartridge 21 is thereafter refilled from the water reservoir 1 through conduit 26 and the throttle arrangement 27 until approximately atmospheric pressure is attained in the cartridge 21, (a slight vacuum is normally present in the cartridge 21).

When the level indicator 75 registers that deaeration is necessary, this is attained by opening the valves 80 and 31 at the same time that the valve 64 is closed. Otherwise, the function is identical to that which has been described in connection with FIG. 5.

In FIG. 6 it is shown that the separation chamber has been provided with a particular conical inlet 85 which faces upwardly. The concentrate thus flows upwardly through the inlet 85 with continuously diminishing velocity. The surface at the upper end of the inlet 85 is as large as the ring surface exterior of the upper end of the outlet so that the concentrate flows around the edge and continues downwardly without increasing the flow velocity. The flow velocity decreases further during the transport downwardly to the outlet 74. This flow pattern is favourable for separating gas bubbles in the flowing liquid.

Figure 7:
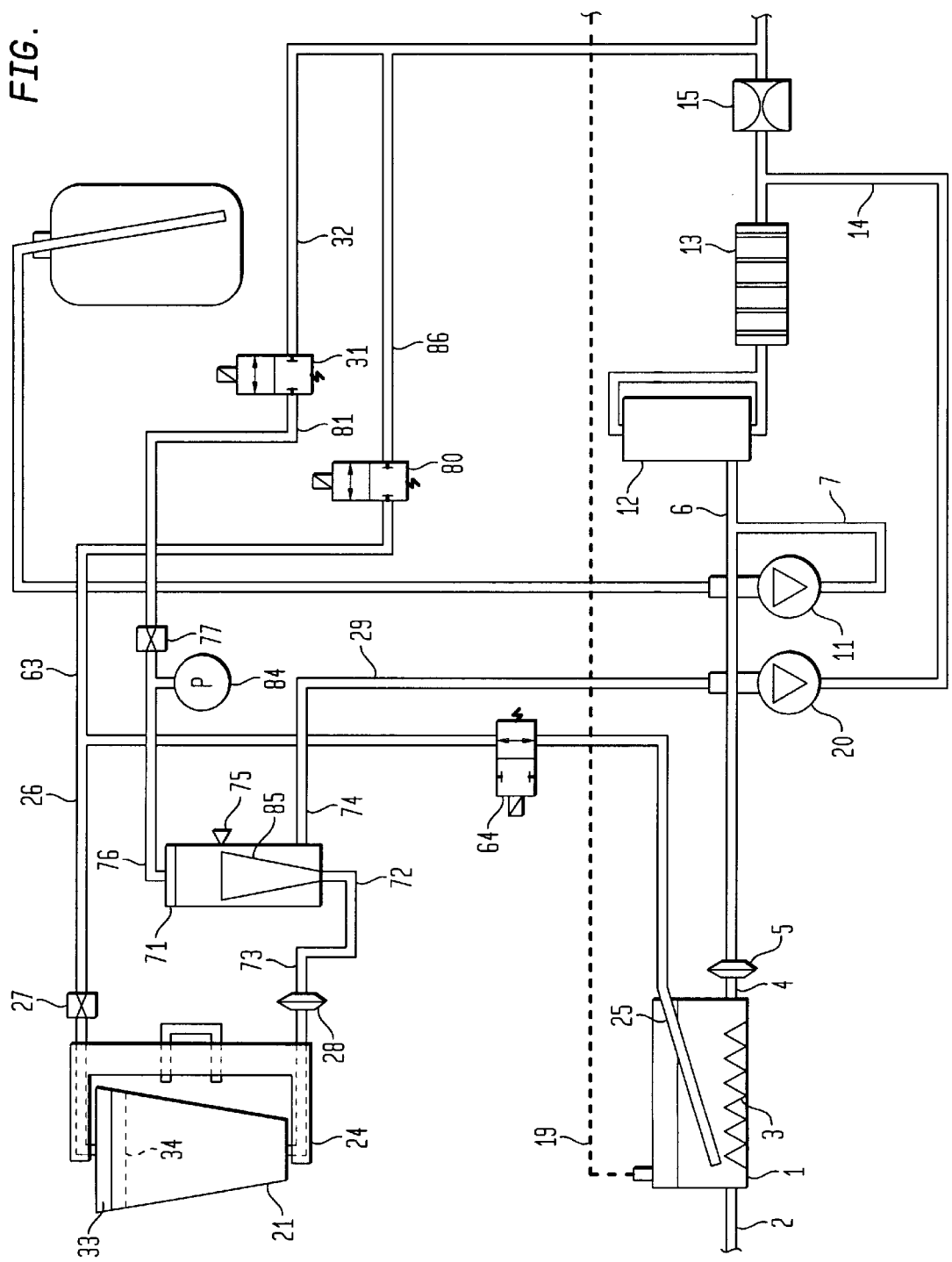
FIG. 7 is a schematic diagram corresponding to FIG. 6 but with an alternative valve arrangement.

An alternative embodiment is shown in FIG. 7 in which the valve 80 is connected directly to the conduit 32 instead of through valve 31. An evacuation conduit 86 connects the conduit 32 to the valve 80 and further to the conduit 63. In this manner, the valves 80 and 31 can be controlled totally independently of each other.

During normal priming in the embodiment according to FIG. 7, the valve 64 is first closed while the valve 31 is open. In this manner, it is ensured that a substantial vacuum is attained in the cartridge 21 before water is supplied through the opening of the valve 64. In this manner, an improved filling of the cartridge during priming is attained.

The present invention has been described above in connection with preferred embodiments of the invention, suitable for use in the dialysis machine known as GAMBRO AK 100. The invention can, of course, be adapted to other types of dialysis machines, for example where an overpressure is present in the bicarbonate cartridge 21.

The present invention has also been described in connection with use of the internal feed pump for the elimination of the gases. Naturally, a separate pump can be used if this should be desired.

The gas separation chamber performs two functions; on the one hand it serves as an indicator for when the cartridge requires gas elimination and, on the other hand, it performs deaeration of the concentrate which is obtained from the cartridge so that a more accurate dosage can be obtained in the dosage pump and noise can be eliminated in the conductivity meter. The latter-mentioned property can also be performed separately without the chamber being used for indication, for example by elimination of gases occurring time-dependently, for example every half hour.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. Apparatus for the elimination of gases from a container including an upper end and a lower end for preparing a concentrate of a powder in water, said apparatus comprising a supply conduit for supplying water to said container, a removal conduit for removing said concentrate from said container, a pump including a negative pressure side, an evacuation conduit for connecting said negative pressure side of said pump with said container, an actuatable valve disposed in said evacuation conduit whereby upon actuation said actuatable valve connects said container with said negative pressure side of said pump, wherein said actuatable valve comprises a three-way valve normally connecting said supply conduit to said upper end of said container.

2. The apparatus of claim 1 wherein said powder comprises a bicarbonate powder and said concentrate comprises a dialysis solution.

3. The apparatus of claim 1 wherein said three-way valve is disposed in proximity to said upper end of said container.

4. The apparatus of claim 1 including a gas separator in said removal conduit, said gas separator including a gas level indicator for indicating a predetermined level of gas in said gas separator.

5. The apparatus of claim 4 wherein said gas separator comprises a chamber having a predetermined cross-sectional area, an inlet proximate to said lower end of said container, and an outlet distal from said lower end of said container, said cross-sectional area of said chamber being substantially greater than the area of said removal conduit whereby the flow velocity through said chamber is substantially lower than the flow velocity through said removal conduit and gas separation takes place therein.

6. The apparatus of claim 5 including a concentrate dosage pump disposed in said removal conduit downstream of said gas separator with respect to said container.

7. The apparatus of claim 1, further comprising an indicator for indicating when said container includes a predetermined amount of said gases, and control means for actuating said actuatable valve in response to said indicator to eliminate said gases from said container.

8. Apparatus for the elimination of gases from a container including an upper end and a lower end for preparing a concentrate of a powder in water, said apparatus comprising a supply conduit for supplying water to said container, a removal conduit for removing said concentrate from said container, a pump including a negative pressure side, an evacuation conduit for connecting said negative pressure side of said pump with said container, an actuatable valve disposed in said evacuation conduit whereby upon actuation said actuatable valve connects said container with said negative pressure side of said pump, said actuatable valve including at least three connections, and wherein said evacuation conduit includes a first evacuation conduit portion connecting said supply conduit to one of said at least three connections, a second evacuation conduit portion connecting said removal conduit to another of said at least three connections, and a third evacuation conduit portion connecting said negative pressure side of said pump to another of said at least three connections, whereby said actuatable valve normally connects said third evacuation conduit portion to said second evacuation conduit portion, and upon actuation said actuatable valve connects said third evacuation conduit portion to said first evacuation conduit portion.

9. The apparatus of claim 8 wherein said supply conduit includes a constriction disposed in said supply conduit distal from said first evacuation conduit portion with respect to said upper end of said container.

10. The apparatus of claim 8 including a supply conduit valve disposed in said supply conduit distal from said first evacuation conduit portion with respect to said upper end of said container, said supply conduit valve being normally open but being closable upon actuation of said actuatable valve during said elimination of said gases.

11. Apparatus for the elimination of gases from a container including an upper end and a lower end for preparing a concentrate of a powder in water, said apparatus comprising a supply conduit for supplying water to said container, a removal conduit for removing said concentrate from said container, a pump including a negative pressure side, an evacuation conduit for connecting said negative pressure side of said pump with said container, a first actuatable valve disposed in said evacuation conduit, whereby upon actuation said first actuatable valve connects said container with said negative pressure side of said pump, and a second actuatable valve connecting said supply conduit to said upper end of said container when said first actuatable valve is closed.

* * * * *